(12) United States Patent
Wangerin et al.

(10) Patent No.: US 8,575,555 B2
(45) Date of Patent: Nov. 5, 2013

(54) NUCLEAR MEDICINE IMAGING SYSTEM AND METHOD USING MULTIPLE TYPES OF IMAGING DETECTORS

(75) Inventors: Kristen Ann Wangerin, Niskayuna, NY (US); Evren Asma, Waterford, NY (US); Jorge Uribe, Niskayuna, NY (US); Ravindra Manjeshwar, Glenville, NY (US)

(73) Assignee: General Electric Company, Niskyuna, NY (US)

( * ) Notice: Subject to any disclaimer, the term of this patent is extended or adjusted under 35 U.S.C. 154(b) by 299 days.

(21) Appl. No.: 13/077,540

(22) Filed: Mar. 31, 2011

(65) Prior Publication Data

US 2012/0248320 A1 Oct. 4, 2012

(51) Int. Cl.
*G01T 1/166* (2006.01)
(52) U.S. Cl.
USPC .................................................. 250/363.05
(58) Field of Classification Search
CPC ... G01T 1/1603; G01T 1/1606; G01T 1/1644; A61B 6/037
USPC ........................................ 250/363.05, 363.04
See application file for complete search history.

(56) References Cited

U.S. PATENT DOCUMENTS

| | | | |
|---|---|---|---|
| 6,303,935 B1 | 10/2001 | Engdahl et al. | |
| 7,233,002 B2 | 6/2007 | Ohana et al. | |
| 2002/0008204 A1* | 1/2002 | Stark | 250/363.08 |
| 2010/0294941 A1* | 11/2010 | Chuang et al. | 250/363.04 |
| 2011/0026685 A1* | 2/2011 | Zilberstein et al. | 378/197 |

* cited by examiner

*Primary Examiner* — Constantine Hannaher
(74) *Attorney, Agent, or Firm* — Jenifer Haeckl

(57) ABSTRACT

A Nuclear Medicine (NM) imaging system and method using multiple types of imaging detectors are provided. One NM imaging system includes a gantry, at least a first imaging detector coupled to the gantry, wherein the first imaging detector is a non-moving detector, and at least a second imaging detector coupled to the gantry, wherein the second imaging detector is a moving detector. The first imaging detector is larger than the second imaging detector and the first and second imaging detectors have different detector configurations. The NM imaging system further includes a controller configured to control the operation of the first and second imaging detectors during an imaging scan of an object to acquire Single Photon Emission Computed Tomography (SPECT) image information such that at least the first imaging detector remains stationary with respect to the gantry during image acquisition.

28 Claims, 6 Drawing Sheets

ND METHOD USING MULTIPLE TYPES OF
NUCLEAR MEDICINE IMAGING SYSTEM AND METHOD USING MULTIPLE TYPES OF IMAGING DETECTORS

BACKGROUND

The subject matter disclosed herein relates generally to Nuclear Medicine (NM) imaging systems, and more particularly to Single Photon Emission Computed Tomography (SPECT) imaging systems with multiple detectors on a gantry.

In NM imaging, such as SPECT imaging, radiopharmaceuticals are administered internally to a patient. Detectors (e.g., gamma cameras), typically mounted on a gantry, capture the radiation emitted by the radiopharmaceuticals and this information is used to form images. The NM images primarily show physiological function of, for example, the patient or a portion of the patient being imaged.

Conventional SPECT imaging systems include one, two or three gamma cameras mounted to a single gantry. The gamma cameras (also referred to as heads) are formed from particular materials. In the selection of material, tradeoffs must be made, such as imaging sensitivity, size, cost, etc. Additionally, specific collimation may be provided, which typically limits the application of the scanner to a particular type of scan, such as whole body bone exams, cardiac exams, etc. Thus, conventional SPECT imaging systems have limitations in design and/or operational characteristics. Moreover, there is limited flexibility in these imaging systems, such that if different scans are to be performed, different scanners often must be used or multiple scans performed.

BRIEF DESCRIPTION

In accordance with an embodiment, a Nuclear Medicine (NM) imaging system is provided that includes a gantry, at least a first imaging detector coupled to the gantry, wherein the first imaging detector is a non-moving detector, and at least a second imaging detector coupled to the gantry, wherein the second imaging detector is a moving detector. The first imaging detector is larger than the second imaging detector and the first and second imaging detectors have different detector configurations. The NM imaging system further includes a controller configured to control the operation of the first and second imaging detectors during an imaging scan of an object to acquire Single Photon Emission Computed Tomography (SPECT) image information such that at least the first imaging detector remains stationary with respect to the gantry during image acquisition.

In accordance with another embodiment, a hybrid imaging system is provided that includes a gantry, at least one Sodium Iodide (NaI) detector coupled to the gantry and at least one Cadmium Zinc Telluride (CZT) detector coupled to the gantry, wherein the NaI detector is larger than the CZT detector. The hybrid imaging system further includes a controller configured to control (1) orbiting movement of the NaI detector and the CZT detector and (2) local movement of the CZT detector to acquire Single Photon Emission Computed Tomography (SPECT) image information from an object during an imaging scan.

In accordance with yet another embodiment, a method for providing an imaging portion of a Nuclear Medicine (NM) imaging system is provided. The method includes providing a gantry for the imaging portion of the NM imaging system, coupling at least a first detector to the gantry for the imaging portion of the NM imaging system and coupling at least a second detector to a gantry for the imaging portion of the NM imaging system. The first detector is larger than the second detector and the first and second detectors have different configurations. The first and second detectors are configured to acquire Single Photon Emission Computed Tomography (SPECT) image information.

DETAILED DESCRIPTION

Figure 1:
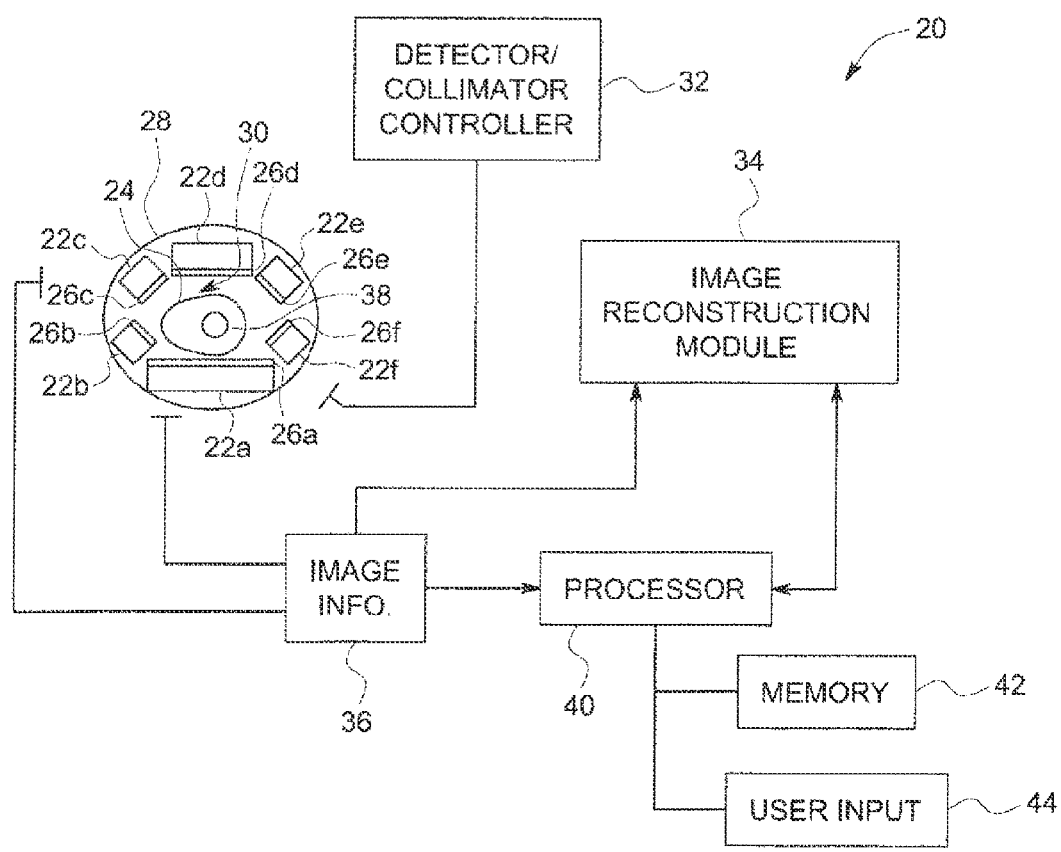
FIG. 1 is a simplified schematic block diagram illustrating a Nuclear Medicine (NM) imaging system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a diagnostic imaging system, and in particular, a Nuclear Medicine (NM) imaging system having a gantry with a plurality of different types of imaging detectors mounted thereto. For example, in various embodiments of an NM imaging system, a hybrid Single Photon Emission Computed Tomography (SPECT) imaging scanner is provided that includes a plurality of detectors with a combination of different types of detectors that acquire SPECT image information. The various embodiments may include detectors formed from different materials, having different configurations or arrangements, having different collimation, etc. The multi-headed hybrid SPECT system may be configured to perform single isotope or multi-isotope imaging. By practicing at least one embodiment, and at least one technical effect is that enhanced or optimized imaging can be provided using the different detector types operating in multiple modes.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects other than people.

A NM imaging system 20 may be provided as illustrated in FIG. 1 having a plurality of NM cameras configured as SPECT detectors 22a-22f. It should be noted that the various embodiments are not limited to the NM imaging system 20 having six detectors 22 as shown or to the sizes or shapes of the detectors 22. For example, the NM imaging system 20 may include more or less detectors 22 having different shapes and/or sizes, or formed from different materials. The NM imaging system 20 in various embodiments is configured as a hybrid SPECT system having a plurality of detectors 22, wherein at least two of the detectors are formed from different materials, have different configurations or arrangements, have different collimation, or are otherwise different.

In operation, an object, such as a patient 24, is positioned in proximity to the one or more of the detectors 22 for imaging. For example, SPECT imaging of the patient 24 is performed by one or more of the detectors 22. The imaging by each of the detectors 22 may be performed simultaneously, concurrently or sequentially.

In the multi-detector camera arrangement, the position of the detectors 22 may be varied, including the relative position between detectors 22, tilt, angle, swivel, etc. of the detectors 22. Additionally, each of the detectors 22 may have a corresponding collimator 26a-26f mounted or coupled thereto. The collimators 26a-26f likewise may be of different types as described in more detail below. Accordingly, one or more detectors 22 may be coupled to a different type of collimator 26 (e.g., parallel hole, pin-hole, fan-beam, cone-beam, etc.). Accordingly, in various embodiments, the detector 22 and collimator 26 together form a module.

The detectors 22 may be single crystal detectors or pixelated detectors that are configured to acquire SPECT image data. For example, the detectors 22 may be formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum (III) bromide (LaBr$_3$), among others.

Additionally suitable components may be provided. For example, the NaI detectors 22 may be coupled to photosensors, such as an array of Photo-Multiplier Tubes (PMTs), an Avalanche Photodiode Detector (AFD), etc.

The detectors 22 may be provided in different arrangements, for example, an "L" mode arrangement, an "H" mode arrangement, or a three or more headed camera arrangement, among others. Additionally, in various embodiments, a single gantry 28 supports the detectors 22 and may be configured in different shapes. Accordingly, although the gantry 28 is illustrated having a circular cross section that defines a bore 30 in which a portion of the patient 24 is inserted, the gantry 28 may take different shapes and configurations, such as a "C" shape.

The imaging system 20 also includes a detector/collimator controller 32 that operates to control the movement of the detectors 22 and/or the collimators 26. For example, the detector/collimator controller 32 may control movement of the detectors 22, such as to rotate or orbit the detectors 22 around a patient, and which may also include moving the detectors closer or farther from the patient 24 and pivoting/swiveling the detectors 22, such that more localized movements or motions are provided. The detector/collimator controller 32 may also optionally control movement of the collimators 26, such as independently of the detectors 22. It should be noted that one or more the detectors 22 and/or the collimators 26 may move during imaging operation, move prior to, but remain stationary during imaging operation, or may remain in a fixed positioned or orientation.

It also should be noted that the detector/collimator controller 32 may be a single unit controlling movement of both the detectors 22 and the collimators 26, may be separate units, or may be a single unit controlling only operation of the detectors 22 or may be a single unit controlling only operation of the collimators 26.

The imaging system 20 also includes an image reconstruction module 34 configured to generate images from acquired image information 36 received from the detectors 22. For example, the image reconstruction module 34 may operate using NM image reconstruction techniques to generate SPECT images of the patient 24, which may include an object of interest, such as the heart 38 of the patient. The image reconstruction techniques may be determined based on the type of detector 22 acquiring the image information 36.

Variations and modifications to the various embodiments are contemplated. For example, in a multi-headed system, namely a system having two or more detectors 22, each detector 22 may be formed from different materials and have different collimators 26. Accordingly, in at least one embodiment, one detector/collimator combination may be configured to obtain information for an entire field of view (FOV), such as the entire spine, while another detector/collimator combination is configured to focus on a smaller region of interest (ROI) to provide higher quality information (e.g., more accurate photon counting). Additionally, information acquired by one detector/collimator combination may be used to adjust the position, orientation, etc. of at least one other detector/collimator combination during imaging.

The image reconstruction module 34 may be implemented in connection with or on a processor 40 (e.g., workstation) that is coupled to the imaging system 20. Optionally, the image reconstruction module 34 may be implemented as a module or device that is coupled to or installed in the processor 40.

The image information 36 received by the processor 40 may be stored for a short term (e.g., during processing) or for a long term (e.g., for later offline retrieval) in a memory 42. The memory 42 may be any type of data storage device, which may also store databases of information. The memory 42 may be separate from or form part of the processor 40. A user input 44, which may include a user interface selection device, such as a computer mouse, trackball and/or keyboard is also provided to receive a user input.

Thus, during operation, the output from the detectors 22, which may include the image information 36, such as projection data from a plurality of detector/gantry angles is transmitted to the processor 40 and the image reconstruction module 34 for reconstruction and formation of one or more images.

Different combinations and variations of detectors 22 and/or collimators 26 will now be described. It should be noted that the various embodiments are not limited to a particular detector, collimator, or detector/collimator combination, but may include any imaging system having a plurality of different types of detectors 22 and/or collimators 26, for example, having at least two detectors 22 of a different type or design. Additionally, the number of detectors 22 and the arrangement thereof may be varied as desired or needed, for example, based on the type of imaging to be performed or the type of image information to be acquired. Accordingly, various embodiments include the imaging system 20 having a plurality of detectors 22, wherein at least two of the detectors 22 are different and are configured to perform imaging of the patient 24 (or other object).

Figure 2:
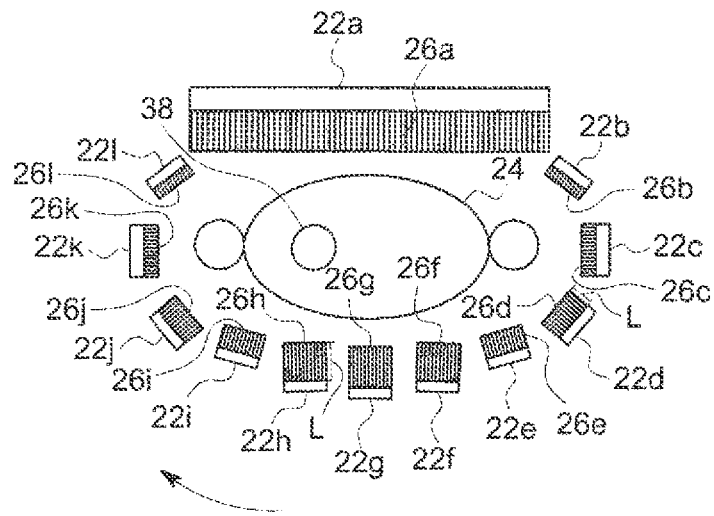
FIG. 2 is a simplified schematic block diagram illustrating different types of detectors in accordance with one embodiment.

For example, in one embodiment, illustrated in FIG. 2, a configuration is provided having one detector 22a formed from one material and the remaining detectors 22b-22l formed from a different material. In the illustrated embodiment, the detector 22a is formed from a NaI material and the remaining detectors 22b-22l are formed from a CZT material. Accordingly, in this configuration, a single NaI detector 22a and a plurality of CZT detectors 22b-22l are provided. The detectors 22a-22l may be sized and shaped the same or differently. For example, in the embodiment illustrated in FIG. 2, the NaI detector 22a is larger than each of the CZT detectors 22b-22l, such that the NaI detector 22a can image the entire patient 24 and the CZT detectors 22b-22l are configured to focus on a portion of the patient 24, such as the heart 38. In this embodiment, one or more of the CZT detectors 22b-22l may be positioned and oriented at different angles or tilted differently to provide focused imaging. However, one or more of the CZT detectors 22b-22l may be angled or tilted the same. In the embodiment of FIG. 2, the CZT detectors 22b-22l are angled such that together the CZT detectors 22b-22l focus on the overall body of the patient 24, instead of on a particular ROI, such as the heart 38. Thus, one or more detectors 22 may be arranged and configured to cover an entire FOV of an imaged, while one or more other detectors are arranged and configured to cover a focused FOV within the object.

It should be noted that as used herein, a set of detectors is generally referred to as the detectors 22 and a set of collimators is generally referred to as the collimators 26. Moreover, the use of letter designations after the numeral designation for the detectors 22 and collimators 26 are used for ease of illustration and do not necessarily represent the same detectors 22 or collimators 26 in the various embodiments or Figures. Thus, the letter designation represents the relative positioning of the detectors 22 or collimators 26 and not necessarily the type or kind of detector.

Additionally, the size and shape of the detectors 22 may be varied as desired or needed. For example, in one embodiment, a NaI detector 22 has dimensions of about 40 cm×50 cm, while a plurality of CZT detectors 22 has dimensions of 8 cm×8 cm each. The dimensions are merely exemplary and are intended only to illustrate that one of the detectors 22 is generally larger in size than the other detectors. Thus, one of the detectors 22 may be a percentage larger than another detector 22, such as 10% larger, 20% larger, 25% larger, 50% larger, 75% larger, or any other amount. It should be noted that the smaller detectors 22 may be of any size, but in various embodiments are each smaller than the larger detector 22.

In FIG. 2, the collimators 26a-26l may be the same or may be different. For example, the collimator 26a may be of a first type, such as a parallel hole collimator, while the collimators 26b-26l may have different types (e.g., converging, diverging, pinhole, slit/slat, fan-beam or cone-beam) based on a desired or required sensitivity or resolution, as well as the position and orientation of the detector 22 on which the collimator 26 is coupled. Thus, the collimators 26 may be of any type. Accordingly, two or more of detectors 22 may have collimators 26 with a different design, which can include a different type, collimator hole aperture (e.g., shape or angle), collimator length, etc. As can be seen in FIG. 2, in one embodiment, one set of collimators 26f-26h have longer collimator holes than another set of collimators 26d, 26e, 26i and 26j, which have longer collimator holes than another set of collimators 26c and 26k, which have longer collimator holes than the collimators 26a and 26l. The collimators 26 may be varied such that, for example, the lengths of the collimator holes may be incrementally varied in a stepwise manner, interleaved, etc.

Figure 3:
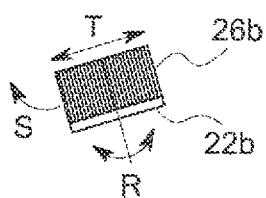
FIG. 3 is a block diagram illustrating movement of a detector in accordance with various embodiments.

Additionally, different types of movements or positioning may be provided. For example, as illustrated in FIG. 3, showing detector 22b with collimator 26b (for illustrative purposes only), the CZT detectors 22b-22l may move all together, in groups, or individually, as well as move together with or independent of the collimators 26b-26l. The movement may include different local movements, for example, translating movement illustrated by the T arrow, swivel movement illustrated by the S arrow and/or rotational movement illustrated by the R arrow.

Accordingly, using a single larger planar NaI detector 22a in combination with multiple smaller CZT detectors 22b-22l, the imaging system 20 can be operated in a plurality of different modes. For example, in one embodiment, the imaging system 20 can be operated in the following modes:

1. A CZT only mode with a small FOV: For small organ imaging such as cardiac applications, imaging is primarily performed using the smaller CZT detectors 22b-22l, which focus on the heart only (a small FOV), resulting in higher sensitivity, as well as higher spatial and energy resolution.

2. Concurrent or simultaneous CZT and NaI acquisition for whole body scan: For large FOV imaging such as whole body bone imaging, imaging is performed using both types of detectors 22. Specifically, the larger NaI detector 22a is positioned in front of the patient 24 and the smaller CZT detectors 22b-22l are positioned and/or oriented around the rest of the body contour of the patient 24 and moved (e.g., swiveled or tilted) to provide tomographic sampling. Tomography images can be reconstructed from data from both types of detectors 22, and the projection from the NaI detector 22a results in a scintigraphy image.

3. NaI planar acquisition to guide CZT focus on smaller FOV: An initial (shorter or rapid) scout scan can be performed using the planar view of the NaI detector 22a to identify regions of interest and the smaller CZT detectors 22b-22l can thereafter be used to focus on the region of interest for high sensitivity, high resolution imaging.

4. Concurrent or simultaneous NaI and CZT acquisition with different FOVs: For a general purpose scan when large coverage and efficient scan time are desired or needed, the two detector types 22a and 22b-22l can be split to concurrently or simultaneously acquire data from different regions of the body.

Thus, in operation, and as example, for small organ imaging like cardiac applications, imaging is primarily performed using one type of detector, for example, the smaller CZT detectors 22b-22l that focus on the heart only, resulting in higher sensitivity, higher spatial and energy resolution. For large FOV imaging, such as whole body bone imaging, imaging is performed using multiple types of detectors, such as the NaI detector 22a and the CZT detectors 22b-22l. Tomographic images can be reconstructed using data from both types of detectors 22a and 22b-22l, with the projection from the NaI detector 22a producing the scintigraphy image. It should again be noted that although this embodiment is described in connection NaI and CZT detectors, other kinds or types of detectors may be used, such as CsI, and LaBr$_3$ based detectors, among others.

Thus, in various embodiments, a hybrid SPECT system is provided with two or more detectors of different types (e.g., different detectors or collimators) that may operate in different modes. The different types of detectors are positioned around the FOV in any type of separated or interleaved design with any type of collimator design. The detectors 22 can be moved (e.g., translated, swiveled or rotated) such that the detectors 22 are positioned optimally for the desired application, for example, to acquire higher resolution image data or information from a particular ROI of interest within a FOV.

It should be realized that although the illustrated embodiment of FIG. 2 includes detectors 22 formed from different materials that are coupled to different collimators 26 with properties or characteristic, the various embodiments are not limited to such different detector and collimator types and combinations. For example, as in various embodiments the detectors 22 may be formed from the same material, but have other differences such that different types of detectors 22 are thereby provided. For example, a plurality of CZT detectors 22 may have different collimation, namely having parallel hole collimators 26 with different collimator hole lengths L (for example, as shown in FIG. 2). In this embodiment, the detectors 22b-22l with corresponding collimators 26b-26l are provided as shown in FIG. 2. However, the NaI detectors 22a of FIG. 2 may be been replaced with a plurality of CZT modules that form the larger detector 22a.

Additionally, as described herein, the detectors 22 can move before or during image acquisition as illustrated in FIG. 3. For example, the detectors 22 may translate, swivel or rotate to thereby provide local movement of the detectors 22, such as before or during image acquisition. However, it should be noted that the detectors 22 in other embodiments may be stationary and mounted in a fixed orientation on the gantry 28 (shown in FIG. 1). It also should be noted that the gantry may move before or during image acquisition to provide orbiting movement of some or all of the detectors 22 (e.g., orbiting movement about the patient 24) as illustrated by the arrow in FIG. 2. Thus, local movement, orbiting movement or a combination thereof may be provided.

As another example, the detectors 22 may include diverging collimators 26, wherein the divergence (e.g., slant angle) of the collimator holes for two or more the collimators 26 may be different. Additionally, the detectors 22 may be mounted at different orientations along the gantry 28. In this embodiment, the detectors 22 may move or may be fixed.

Figure 4:
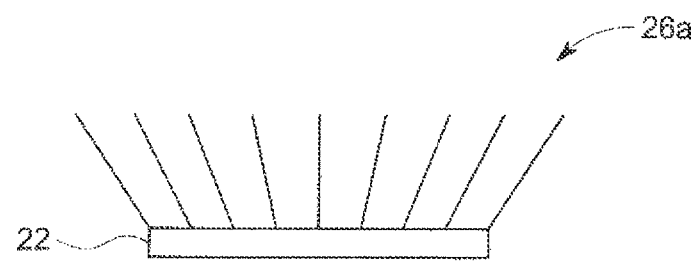
FIG. 4 is a block diagram illustrating a diverging collimator in accordance with one embodiment.
Figure 5:
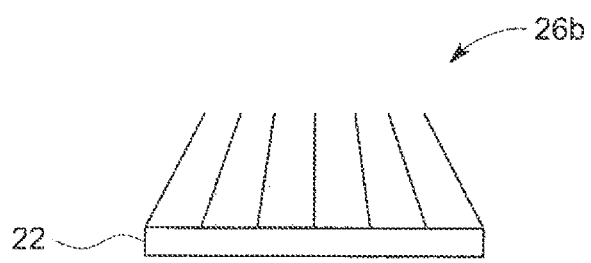
FIG. 5 is a block diagram illustrating a converging collimator in accordance with one embodiment.
Figure 6:
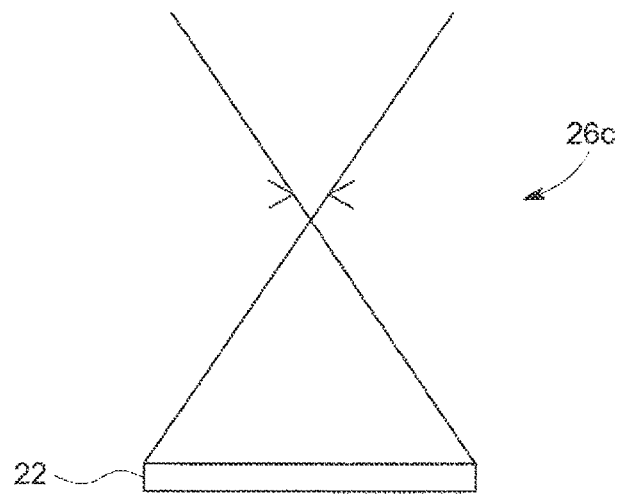
FIG. 6 is a block diagram illustrating a pinhole collimator in accordance with one embodiment.

Other variations are contemplated using the different collimation arrangements described above with detectors 22 formed from different materials. For example, one or more different collimators 26 may be provided in combination with one or more detectors 22, such as diverging collimators 26a as shown in FIG. 4, converging collimators 26b as shown in FIG. 5 and/or one or more pinhole collimators 26c as shown in FIG. 6. However, it should be noted that other collimators 26 or collimation arrangements may be provided as described herein or as otherwise contemplated.

Figure 7:
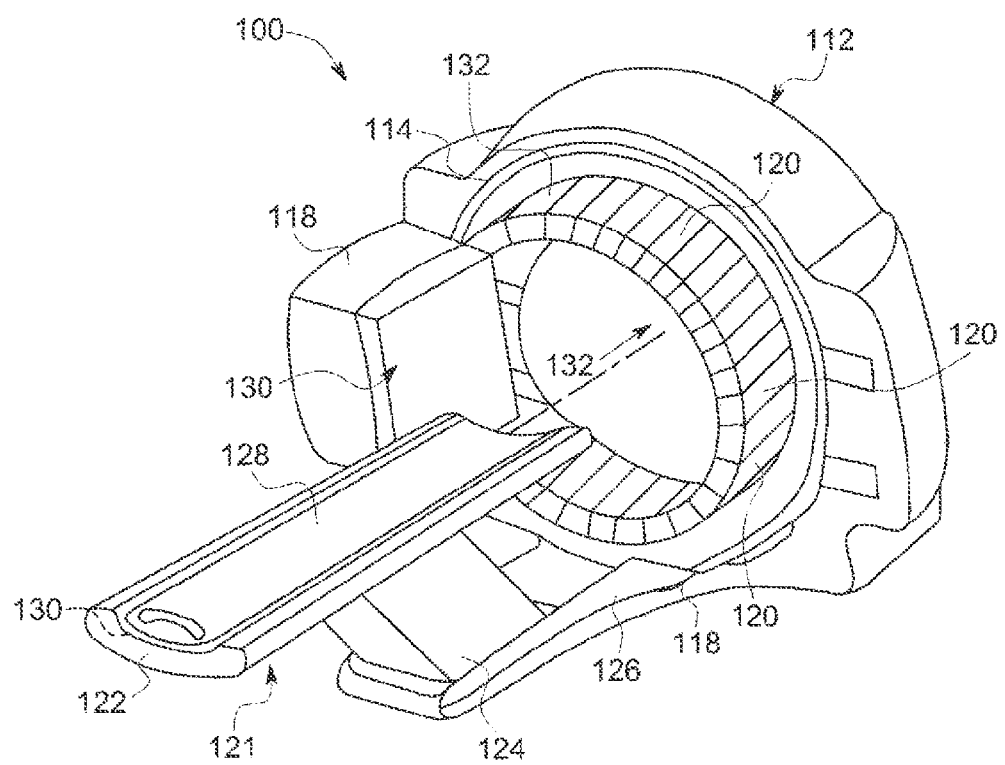
FIG. 7 is a perspective view of an exemplary NM imaging system formed in accordance with various embodiments.

In addition to having different detector and/or collimator arrangements, the different configurations may have different forms of movement. For example, as illustrated in FIG. 3, local movements of the detectors 22 may be provided and/or orbiting movement of the detectors 22 may be provided as illustrated in FIG. 7 and described below. In one embodiment, the gantry 28 (or 112 as shown in FIG. 7) may include a plurality of brackets (not shown) or other suitable mounting structures that may be configured to allow the detectors 22 to rotate about the bore 30, as well as provide other movements for the detectors 22 as described herein.

Additionally, by adding movement of the detectors 22, an increased FOV or radius of image scanning may be provided. For example, detectors 22 with parallel hole collimators 26 may be used wherein movement of the detectors 22 is also utilized, such that a plurality of movements (e.g., five different swivel operations or seven different swivel operations) are performed. As can be appreciated, the additional swivel movements of the detectors 22 provides a larger FOV or radius of scanning, which can be combined with the different detector types to perform imaging.

Thus, various embodiments provide an NM imaging system that includes multiple detector types. In operation, multiple different scanning modes may be provided. For example, multi-mode scanning may be provided wherein a large FOV scanning is performed to provide tomography, along with planar acquisition (scintigraphy) using the different detector types. It should be noted that other imaging protocols or combinations of imaging scans may be provided.

The various embodiments may provide different detector configurations, for example:

(1) at least one first imaging detector having a single larger scintillator type detector and the at least one second imaging detector having a plurality of smaller scintillator type detectors;

(2) at least one first imaging detector having a single larger scintillator type detector and the at least one second imaging detector having a plurality of smaller direct conversion type detectors;

(3) at least one first imaging detector having a single larger direct conversion type detector and the at least one second imaging detector having a plurality of smaller scintillator type detectors; or (4) at least one first imaging detector having a single larger direct conversion type detector and the at least one second imaging detector having a plurality of smaller direct conversion type detectors.

It should be appreciated that other detector configurations may be provided. Additionally, different collimator configurations may be provided or a combination of different detector and/or collimator configuration to provide different module configurations, wherein a module is formed from a detector and collimator combination.

Thus, one larger non-orbiting detector and one or more smaller detectors that can have local motion (e.g. swivel) may be provided, in which these detectors are of different materials (e.g., NaI and CZT), variations and modifications are contemplated. For example, both types of detectors can remain stationary and both may be of the same material. Thus, different configurations may be provided such as, different material and/or different geometry combinations. For example, the detectors 22 may be formed from different materials or may have different designs. In the various embodiments, the detectors 22 may have different pixel patterns, pixel sizes, thicknesses, etc.

In operation, the 32 controller, thus, may be configured to control (1) orbiting movement of the NaI detector and the CZT detector and (2) local movement of the CZT detector to acquire Single Photon Emission Computed Tomography (SPECT) image information from an object during an imaging scan. It should be noted that in one of the detectors, which in one embodiment is the larger NaI detector, is a non-moving detector 22 respect to the gantry 28.

The detectors 22 of the various embodiments may be provided as part of different types of imaging systems, for example, NM imaging systems such as SPECT imaging systems having different detector configurations. For example, FIG. 7 is a perspective view of an exemplary embodiment of a medical imaging system 100 constructed in accordance with various embodiments, which in this embodiment is a SPECT imaging system. The system 100 includes an integrated gantry 112 that further includes a rotor 114 oriented about a gantry central bore 132. The rotor 114 is configured to support one or more NM cameras, which are illustrated as a single NaI camera 118 and a plurality of CZT cameras 120. It should be noted that although the CZT cameras 120 are illustrated as being mounted in sections and having abutting edges in each section, the CZT cameras 120 may be individually mounted and include spacing or gaps therebetween, such as to allow individual movement of the CZT cameras 120. It should be noted that the NaI camera 118 and the CZT cameras 120 may be configured, arranged and/or operated according to any of the embodiments described herein.

The cameras 118 and 120 also include collimators (not shown), which may be configured, arranged and/or operated according to any of the embodiments described herein. The rotor 114 is further configured to rotate axially about an examination axis through the gantry central bore 132.

A patient table 121 may include a bed 122 slidingly coupled to a bed support system 124, which may be coupled directly to a floor or may be coupled to the gantry 112 through a base 126 coupled to the gantry 112. The bed 122 may include a stretcher 128 slidingly coupled to an upper surface 130 of the bed 122. The patient table 121 is configured to facilitate ingress and egress of a patient (not shown) into an examination position that is substantially aligned with the examination axis. During an imaging scan, the patient table 121 may be controlled to move the bed 122 and/or stretcher 128 axially into and out of the bore 132. The operation and control of the imaging system 100 may be performed in any suitable manner. It should be noted that the various embodiments may be implemented in connection with imaging systems that include rotating gantries or stationary gantries.

Figure 8:
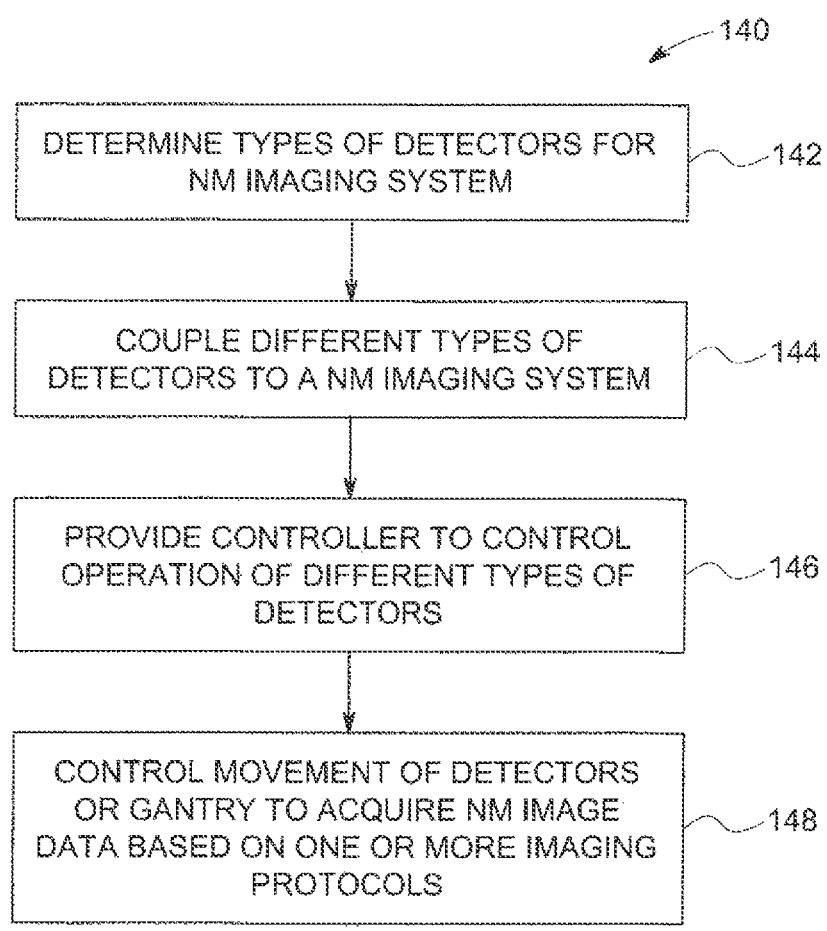
FIG. 8 is a flowchart of a method for manufacturing and operating an imaging portion of an NM imaging system in accordance with various embodiments.

Additionally, various embodiments provide a method 140 as illustrated in FIG. 8 for providing and operating the imaging portion of an NM imaging system. The method 140 includes determining at 140 the types of detectors for the NM imaging system. For example, depending on the types of exam(s) to be performed by the imaging system, the detector material, size, arrangement, etc, and/or collimation arrangement/configuration is selected. Thereafter, the different types of detectors are coupled to the NM imaging system at 144, for example, to a rotor of a gantry of the imaging system. The collimators may be coupled to the detectors prior to or after the detectors have been coupled to the imaging system.

A controller is also provided at 146 for controlling the operation of the different types of detectors and/or collimators as described in more detail herein. The controller may be embodied in software, hardware, or a combination thereof. In operation, the controller may operate to acquire image information from the different types of detectors simultaneously, concurrently or sequentially (e.g., first acquiring a scout scan). For example, at 148 the controller operates to control the movement of the detectors and/or of the gantry to acquired NM image data, such as SPECT image data. The controller may control local movement of the detectors and/or orbiting movement the gantry before or during image acquisition. The movement may be provided based on a particular imaging protocol. In one embodiment, two different SPECT applications or imaging protocols may be provided, such as scintigraphy and tomography. Accordingly, in one embodiment, both two-dimensional and three-dimensional SPECT images may be acquired during a single imaging scan.

It should be noted that other variations and modifications are contemplated. For example, in one embodiment the smaller detectors 22 (e.g., smaller sized CZT detectors) may be grouped together to form a slightly larger detector, that is still smaller than the larger detector (e.g., larger NaI detector). Thus, a plurality of smaller imaging detectors 22 may be combined to form a larger imaging detector 22 that is smaller than, for example, the single larger imaging detector.

Figure 9:
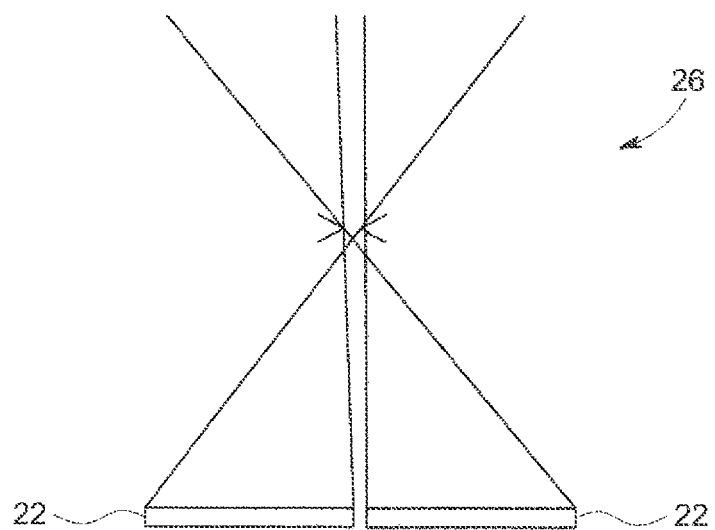
FIG. 9 is a block diagram illustrating a collimator arrangement in accordance with an embodiment.

As another example of a modification, one collimator 26 (e.g., a pinhole collimator) may be assigned to multiple detectors 22 as illustrated in FIG. 9. Thus, in this embodiment, a single collimator 26 is provided in combination with two detectors 22 such that the collimator 26 collimates or "sees" two detectors 22.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A Nuclear Medicine (NM) imaging system comprising:
a gantry;
at least a first imaging detector coupled to the gantry, the first imaging detector being a non-moving detector having a fixed orientation with respect to the gantry;
at least a second imaging detector coupled to the gantry, wherein the second imaging detector is a moving detector, wherein the first imaging detector is larger than the second imaging detector and the first and second imaging detectors comprise different detector configurations; and
a controller configured to control the operation of the first and second imaging detectors during an imaging scan of an object to acquire Single Photon Emission Computed Tomography (SPECT) image information such that at least the first imaging detector remains stationary with respect to the gantry during image acquisition.

2. The NM imaging system of claim 1, wherein the first and second imaging detectors are formed from different materials.

3. The NM imaging system of claim 1, wherein the first imaging detector is famed from a scintillator material and photosensor and the second imaging detector is formed from a direct conversion material.

4. The NM imaging system of claim 1, wherein the gantry comprises a rotor having a bore therethrough and wherein the controller is configured to control orbiting movement of the gantry about the bore.

5. The NM imaging system of claim 1, wherein the controller is configured to control local movement of at least one of the second imaging detectors and not the first imaging detector, and further wherein the first imaging detector is a non-orbiting detector.

6. The NM imaging system of claim 5, wherein the local movement comprises at least one of translating movement, swiveling movement or rotating movement.

7. The NM imaging system of claim 1, wherein the first imaging detector comprises a single planar Sodium Iodide (NaI) detector and the second imaging detector is formed from Cadmium Zinc Telluride (CZT).

8. The NM imaging system of claim 7, further comprising a plurality of additional imaging detectors formed from CZT.

9. The NM imaging system of claim 1, wherein the first and second imaging detectors acquire the SPECT image information and further comprising an image reconstruction module configured to form a tomography image and a scintigraphy image, respectively.

10. The NM imaging system of claim 1, wherein the first and second imaging detectors acquire image information concurrently.

11. The NM imaging system of claim 1, wherein the first and second imaging detectors acquire image information sequentially during a single image scan.

12. The NM imaging system of claim 1, further comprising first and second collimators coupled to the first and second imaging detectors, wherein the first and second collimators being of different types to form the different types of imaging module with the imaging detectors.

13. The NM imaging system of claim 12, wherein the first and second collimators comprise at least one of a parallel hole collimator, a diverging collimator, a converging collimator, a slit/slat collimator, a pinhole collimator, a fan-beam collimator or a cone-beam collimator.

14. The NM imaging system of claim 12, wherein the first and second collimators have at least one of different collimator hole apertures or collimator lengths.

15. The NM imaging system of claim 1, wherein the different detector configurations comprise at least one first imaging detector having a single larger scintillator type detector and the at least one second imaging detector having a plurality of smaller scintillator type detectors.

16. The NM imaging system of claim 1, wherein the different detector configurations comprise at least one first imaging detector having a single larger scintillator type detector and the at least one second imaging detector having a plurality of smaller direct conversion type detectors.

17. The NM imaging system of claim 1, wherein the different detector configurations comprise at least one first imaging detector having a single larger direct conversion type detector and the at least one second imaging detector having a plurality of smaller scintillator type detectors.

18. The NM imaging system of claim 1, wherein the different detector configurations comprise at least one first imaging detector having a single larger direct conversion type detector and the at least one second imaging detector having a plurality of smaller direct conversion type detectors.

19. The NM imaging system of claim 1, further comprising a plurality of smaller second imaging detectors combined to form a larger imaging detector that is smaller than the first imaging detector.

20. The NM imaging system of claim 1, further comprising at least a collimator assigned to multiple imaging detectors.

21. A hybrid imaging system comprising:
a gantry;
at least one Sodium Iodide (NaI) detector coupled to the gantry;
at least one Cadmium Zinc Telluride (CZT) detector coupled to the gantry, wherein the NaI detector is larger than the CZT detector; and
a controller configured to control (1) orbiting movement of the NaI detector and the CZT detector and (2) local movement of the CZT detector to acquire Single Photon Emission Computed Tomography (SPECT) image information from an object during an imaging scan.

22. The hybrid imaging system of claim 21, wherein the image information is acquired one of simultaneously or concurrently from the NaI detector and the CZT detector.

23. The hybrid imaging system of claim 21, wherein the image information is acquired sequentially from the NaI detector and the CZT detector.

24. The hybrid imaging system of claim 21, further comprising collimators coupled to the NO detector and the CZT detector, wherein the collimators are different.

25. A method for providing an imaging portion of a Nuclear Medicine (NM) imaging system, the method comprising:
providing a gantry for the imaging portion of the NM imaging system;
coupling at least a first detector to the gantry for the imaging portion of the NM imaging system; and
coupling at least a second detector to the gantry for the imaging portion of the NM imaging system, wherein the first detector is larger than the second detector and the first and second detectors have different detector configurations, such that the first and second detectors are configured to acquire Single Photon Emission Computed Tomography (SPECT) image information, wherein the first and second detectors are formed from different materials.

26. The method of claim 25, further comprising coupling collimators to the first and second detectors, wherein the collimators being of different types.

27. The method of claim 25, wherein coupling one of the first or second detectors to the gantry, comprises fixedly coupling one of the first or second detectors to the gantry to have a fixed orientation with respect to the gantry.

28. The method of claim 25, further comprising controlling movement of the detectors, wherein an orbiting movement of both detectors is controlled using the gantry and a local movement of the second detector is controlled.

* * * * *